United States Patent [19]

McCracken et al.

[11] 4,413,621
[45] Nov. 8, 1983

[54] FILM DRESSING

[75] Inventors: Robert W. McCracken, Westfield; James P. Dellas, East Brunswick, both of N.J.

[73] Assignee: Johnson & Johnson Products, Inc., New Brunswick, N.J.

[21] Appl. No.: 329,970

[22] Filed: Dec. 11, 1981

[51] Int. Cl.³ .............................................. A61F 13/02
[52] U.S. Cl. ..................... 128/156; 128/155; 604/390
[58] Field of Search ............... 128/155, 156; 604/389, 604/390; 424/261, 40, 41; 428/43

[56] References Cited

U.S. PATENT DOCUMENTS

| 3,645,835 | 2/1972 | Hodgson | 428/355 |
| 4,122,552 | 10/1983 | Tedford | 604/389 |
| 4,281,650 | 8/1981 | Spiegelberg | 128/156 |
| 4,302,500 | 11/1981 | Flora | 428/284 |
| 4,346,700 | 8/1982 | Dunshee et al. | 128/155 |

FOREIGN PATENT DOCUMENTS 51935 5/1982 European Pat. Off. ............ 128/156

Primary Examiner—Richard J. Apley
Assistant Examiner—Sherri Vinyard
Attorney, Agent, or Firm—Michael Q. Tatlow

[57] ABSTRACT

A high moisture vapor permeable film dressing with an adhesive backing and a release sheet are disclosed. The dressing has two opposed side edges which are free of adhesive and a perforation through the adhesive near the side edge to allow the dressing to be applied to the patient and the adhesive-free edges removed, which prevents the edges of the dressing from rolling off the patient and dislodging the dressing.

4 Claims, 6 Drawing Figures

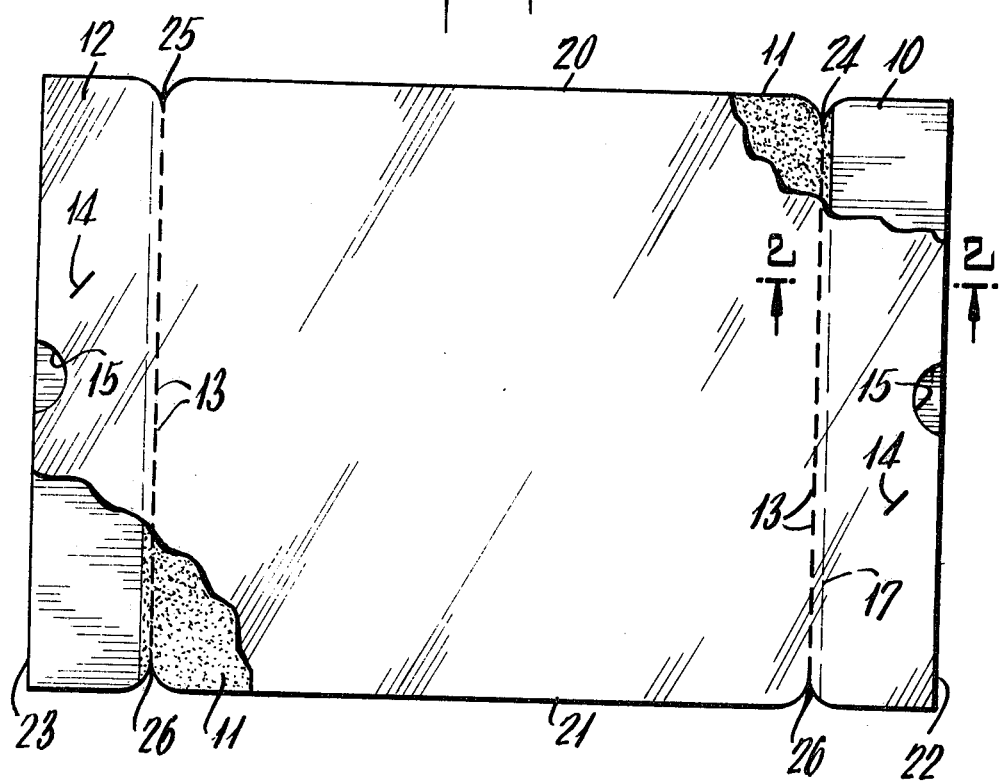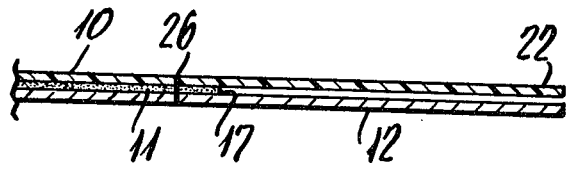

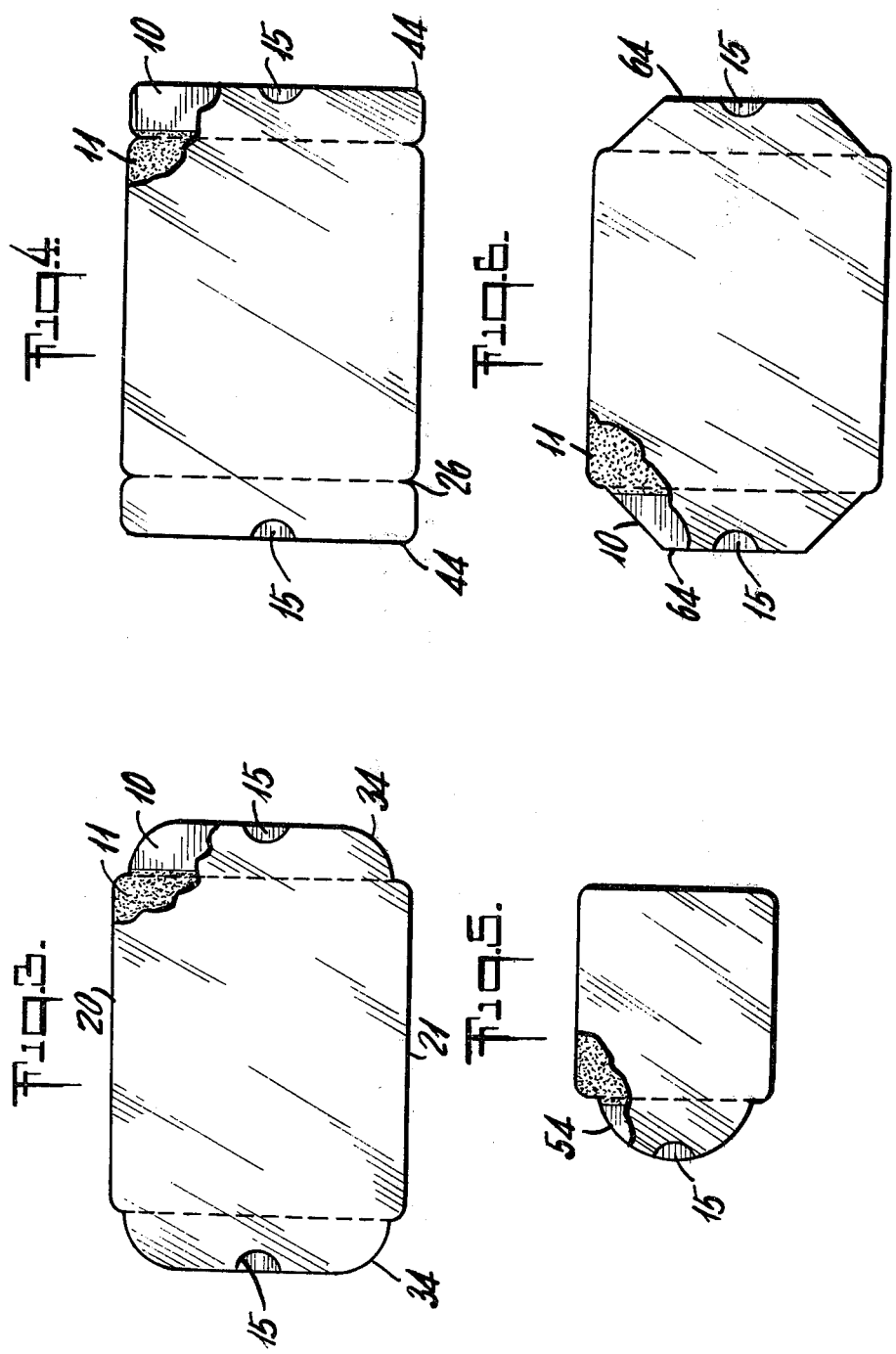

FILM DRESSING

FIELD OF THE INVENTION

The present invention relates to surgical dressings made from films which are oxygen permeable, have high moisture vapor permeability but which are impermeable to liquid water and bacteria.

PRIOR ART

Surgical dressings made with composite layers of film and adhesive which have high moisture vapor transmission rates have been disclosed in U.S. Pat. Nos. 3,483,018 and 3,645,835. These dressings are made from films which may be transparent and which have moisture vapor transmission rates of greater than 15 grams per 100 square inches per 24 hours. These dressings are used in many applications and have an advantage in that they are impervious to bacteria and liquid water but yet allow oxygen to penetrate the dressing from the ambient atmosphere and allow moisture from the skin of the patient to escape from beneath the dressing.

The operative body contact area of these dressings are made of continuous films, that is, films which are not perforated or are not microporous. The adhesive coating which is applied to these dressings also must have a moisture vapor transmission rate which is sufficient to allow the composite dressing to have a moisture vapor transmission rate of at least 15 grams per 100 square inches per 24 hours.

In order to obtain the desired moisture vapor transmission rate, the dressings are made from extremely thin films of polyurethane or of other polymeric materials which have the desired moisture vapor transmission properties. These films are extremely thin, less than 10 mils, and are very flexible, limp and flimsy because of their thinness. These characteristics allow the dressing to be applied to the varying contours of the human body but also create some problems in the application of the dressing to a patient. The dressings are manufactured with a release sheet covering the adhesive surface of the dressing. The release sheet is removed from the dressing when the dressing is applied to the patient. The thinness of the film and its flexibility allows the film to turn over onto itself during attempts to apply the film dressing to a patient. The film is similar in this property to polyvinylidene chloride film household wrap. When a portion of adhesive surfaces of the film touch other portions of the adhesive surface, the film dressing sticks to itself and makes it extremely difficult to apply to the patient.

In order to overcome this problem, the film dressings of the type are made with adhesive-free tabs at opposite ends of the film. In some products there is a reinforcing member at the tab ends to provide a grasping or holding surface to be used to apply the dressings to a patient. After the dressing is applied, the adhesive-free tab end is cut off the adhesive portion of the dressing with scissors or by tearing the film. The use of scissors or tearing tends to leave a ragged or uneven edge on the film dressing. This uneven edge tends to roll off the skin of the patient and, eventually, the entire dressing may be inadvertently removed from the patient.

SUMMARY OF THE INVENTION

The present invention is directed to a film dressing which eliminates the tab removal problems of the prior art film dressings. The present dressing provides a film dressing in which the tabs are readily removed and in which the tendency to roll the edges of dressing is eliminated.

DETAILED DESCRIPTION OF THE INVENTION

The invention will be better understood with reference to the drawings in which:

FIG. 1 is a plan view of the dressing of the present invention.

FIG. 2 is a cross-sectional view of the dressing taken along lines 2—2 of FIG. 1.

FIGS. 3-6 are alternate embodiments of the present invention.

The moisture vapor permeable film used in the present dressing is made from synthetic polymers which are capable of being formed into continuous films by casting, extrusion or other known film-making processes. The film thickness is from 0.5 to 10 mils and preferably from 1 to 3 mils. The film is continuous in that it has no perforations or pores in the body-contacting portion of the film which extend through the depth of the film. Films of this type are known and generally are hydrophilic, polymeric materials through which water vapor is capable of diffusing. The films that may be used in the present invention are the polyurethane films which are described in U.S. Pat. No. 2,871,218 and the arylate copolymers which are described in U.S. Pat. Nos. 2,949,443 and 3,645,835. Generally, these films will have moisture vapor transmission rates between 15 and 80 grams per 100 square inches per 24 hours, as determined by ASTM Test E96 at 100° F. and 90% Relative Humidity.

The moisture vapor permeable film is shown in the drawing as 10. On one surface of the film is a skin adhesive 11. The particular adhesive that is employed may be selected from one of the well-known skin contact adhesives such as those disclosed in U.S. Pat. Nos. 3,189,581; 3,218,357; 3,325,459 and 4,112,213. These adhesives are generally copolymers of 2-ethylhexyl acrylate and vinyl acetate in ratios of approximately 60 to 70 parts of the acrylate and 30 to 40 parts of the vinyl acetate. The polymers may also contain small amounts of N-tertiary butylacrylamide as a third monomer and a cross-linking agent. The preferred adhesive is a copolymer of approximately 70% 2-ethylexyl acrylate and 30% vinyl acetate and containing from 0.01 to 1% of a silane cross-linking agent as discussed in U.S. Pat. No. 4,112,213. Water based adhesive and hot melt adhesives may also be employed.

The adhesive is deposited on the film by solvent spreading, coating, extrusion or other known method. The level of the adhesive on the film should not be so great that the moisture vapor transmission characteristics of the film are impeded. Generally, a coating level of from 0.5 to 3 ounces per square yard is sufficient to obtain adequate skin adhesion but not so great as to interfere with the moisture vapor transmission characteristics desired in the finished dressing. The adhesive mass may be applied directly to the film or may be applied to a silicone-coated carrier sheet and the film then brought into contact with the adhesive on the carrier sheet. The film may be removed from the carrier sheet for subsequent processing, or the carrier sheet may remain with the film and become the release sheet 12 in the finished dressing.

The release sheet may be partially cut away, as shown in the drawing, by die cutting a semi-circular portion out of the release sheet to provide free film edge 15 to aid in the removal of the film from the release sheet.

As shown in FIG. 1, the dressing has a top edge 20 and a bottom edge 21, and two opposing exterior side edges 22 and 23, and opposing interior side edges formed along the perforation lines 24 and 25. The film 10 of the dressing is coated with adhesive 11 from the top edge to the bottom edge but not to the exterior side edges 22 and 23. This is best shown in FIG. 2. The interior side edges 24 and 25 are formed by a series of perforations 13 which extend through the film. The perforations 13 may also extend partially or completely through the release sheet 12 as a matter of manufacturing convenience, although perforations in the release sheet are not necessary. The perforations are made on straight lines from the top edge to the bottom edges of the film. The ratio of the cut areas of the perforation line to the uncut areas of the perforation line can range from about 6 to 1 to about 0.5 to 1. The preferred ratio is about 3.5 to 1. The perforations should be such that the film can be removed from the carrier sheet without tearing the film along the perforation line, but the perforation line should be readily broken after the film dressing is applied to the skin of the patient.

The portion of the film between the perforation lines 24 and 25 or interior side edge of the film dressing and the exterior side edge 22 or 23 of the dressing is a handling tab 14 which is substantially free of adhesive. The tabs 14 are used to hold the dressing to remove it from the release sheet and to apply the dressing to the patient.

The adhesive 11 is applied to the film to line 17 about 1/16 inch to ⅜ inch beyond the perforation lines 24 or 25 or interior side edges of the dressing. This insures that the adhesive is completely applied to that portion of the dressing which will be applied to the patient. If there is an adhesive free edge on the dressing, that edge will tend to roll off the skin of the patient, and the dressing may be dislodged from the patient.

The corners 26 of the dressing may be rounded to make them less likely to lift and roll off the skin of the patient.

The embodiment of the invention shown in FIGS. 3, 4 and 6 are similar to that shown in FIGS. 1 and 2 but have a handling tabs of a different configuration than that shown in FIG. 1.

In the embodiment of the invention shown in FIG. 3, the handling tabs 34 are shorter in their length than the distance between the top edge 20 and bottom edge 21 of the dressing.

In the embodiment of the invention shown in FIG. 4, the outside edges of the handling tabs 44 are rounded.

In the embodiment of the invention shown in FIG. 5, there is a single handling tab 54. This form of the invention is particularly suitable for dressings of relatively small dimension.

In the embodiment of the invention shown in FIG. 6, the handling tabs 64 are of a different shape than those in FIG. 1 making them more readily identifiable as a handling tab.

In applying the dressing to a patient, one edge of the film is removed from the release sheet. The removed edge is applied to the skin of the patient at a point spaced from the center of the wound area intended to be covered by the dressing. The dressing is then applied to the skin by gentle pressure while removing the remainder of the release sheet. After the dressing is in place, the adhesive-free ends of the dressing are removed to prevent the rolling of the dressing. As the perforations in the dressing are within the adhesive coated area of the dressing, the edges of the dressing will remain in place with no tendency to roll.

A typical dressing of the present invention is made as follows:

A 1.5 mil polyether polyurethane film is coated with an adhesive which is a copolymer of 70% 2-ethylhexyl acrylate and 30% vinyl acetate which contains a small amount, 0.1 to 1%, of a silane cross-linking monomer. The dressing has an overall dimension of 4 by 6 inches. The film is coated over an area 4 by 4½ inches. There is a perforation line on both side edges of the film 1/16 inch inside the area coated with the adhesive. The perforation line is made of alternating 0.115 inch cut portions and 0.033 inch uncut portions.

We claim:

1. An adhesive dressing comprising a transparent polymeric film from 0.6 to 10 mils thick having a moisture vapor transmission rate of at least 15 grams per 100 square inches per 24 hours and being impervious to liquid water, said film having a top edge, a bottom edge and two opposed side edges, a skin-adhering adhesive coating on one side of said film extending from said top edge to said bottom edge and between lines spaced inwardly from said opposed side edges to provide a pair of adhesive-free handling tabs on the side edges of said dressing, a perforation line parallel to each of said side edges and extending through said adhesive coating and said film and a release sheet covering said adhesive coating.

2. The dressing of claim 1 in which there is a semicircular cutout through said release sheet at a side edge of said dressing to expose said film.

3. The dressing of claim 1 in which the film has a thickness of from 1 to 3 mils.

4. An adhesive dressing comprising a transparent film of from 0.6 to 10 mils thick having a moisture vapor transmission rate of at least 15 grams per 100 square inches per 24 hours but being impervious to liquid water, said film having a top edge, a bottom edge and two opposed side edges,
at least one perforation line through said film substantially parallel to a first side edge and spaced inwardly from said first side edge,
a skin-adhering adhesive coating on said film extending from said top edge to said bottom edge and from said second side edge to a line between the perforation line and the first side edge of the dressing to provide an adhesive-free handling tab,
a release sheet covering the adhesive coating.

* * * * *